(12) United States Patent
Opie et al.

(10) Patent No.: US 7,191,900 B2
(45) Date of Patent: Mar. 20, 2007

(54) GUIDE WIRE CONTAINMENT AND DISPENSING APPARATUS

(75) Inventors: John C. Opie, Scottsdale, AZ (US); Stephen J. Joyce, Phoenix, AZ (US); Thomas Izdebski, Phoenix, AZ (US)

(73) Assignee: JS Vascular, Inc., Scottsdale, AZ (US)

( * ) Notice: Subject to any disclaimer, the term of this patent is extended or adjusted under 35 U.S.C. 154(b) by 87 days.

(21) Appl. No.: 10/861,887

(22) Filed: Jun. 3, 2004

(65) Prior Publication Data
US 2005/0020940 A1    Jan. 27, 2005

Related U.S. Application Data

(60) Provisional application No. 60/475,607, filed on Jun. 3, 2003.

(51) Int. Cl.
  B65D 83/10   (2006.01)
  A61M 25/00   (2006.01)
  A61B 5/00    (2006.01)

(52) U.S. Cl. .................. 206/364; 206/63.3; 600/585; 604/159; 604/171; 604/528

(58) Field of Classification Search ........ 206/363–364, 206/63.3, 303, 388, 409, 438–439; 242/160.2, 242/160.4, 166, 170–171, 388.6, 588.3; 600/585; 604/159, 528, 171
See application file for complete search history.

(56) References Cited

U.S. PATENT DOCUMENTS

| | | | | |
|---|---|---|---|---|
| 3,310,167 A | * | 3/1967 | Knox | .......................... 242/171 |
| 4,903,826 A | * | 2/1990 | Pearce | ....................... 206/63.3 |
| 5,125,416 A | * | 6/1992 | Phillips | ....................... 600/585 |
| 5,507,300 A | | 4/1996 | Mukai et al. | |
| 5,730,150 A | | 3/1998 | Peppel et al. | |
| 5,827,202 A | * | 10/1998 | Miraki et al. | ................ 600/585 |
| 5,843,002 A | * | 12/1998 | Pecor et al. | ................. 600/585 |
| 6,086,008 A | * | 7/2000 | Gray et al. | ............... 242/388.6 |
| 6,916,293 B2 | * | 7/2005 | Hamilton | ..................... 600/585 |
| 2002/0157981 A1 | | 10/2002 | Whiting et al. | |

* cited by examiner

Primary Examiner—Bryon P. Gehman
(74) Attorney, Agent, or Firm—Snell & Wilmer L.L.P.

(57) ABSTRACT

The invention is a medical guide wire containment and dispensing device. The device is of unitary construction and defines a single, generally annular opening that receives the guide wire. Preferably, the device includes a mount for retaining a guide-wire torque device.

11 Claims, 7 Drawing Sheets

GUIDE WIRE CONTAINMENT AND DISPENSING APPARATUS

RELATED APPLICATIONS

This application claims priority to U.S. Provisional Application Ser. No. 60/475,607, filed Jun. 3, 2003. The disclosure of U.S. application Ser. No. 10/444,773, filed May 24, 2003, is incorporated herein by reference.

TECHNICAL FIELD OF THE INVENTION

This invention relates to the field of medical guide wires and, more particularly to an improved storage container for medical guide wires.

BACKGROUND OF THE INVENTION

The use of medical guide wires (or "guide wires") is ubiquitous in modern era, non-invasive, medical practice including cardiac catheterization and interventional radiology disciplines and the practice of endo-vascular surgery.

An accepted method of accessing the interior of a blood vessel involves placing a needle inside a short cannula, and then placing the needle and cannula into the blood vessel with subsequent extraction of the needle, but retention of the short cannula. This method is used for both diagnostic and endo-vascular surgical procedures. Once the needle is removed from the blood vessel, the cannula becomes an open access to the vasculature and blood will escape through the cannula unless the cannula is capped. Once a cannula has been placed in a blood vessel using this or any other method, it is common for a general-purpose guide wire, such as a 0.018-inch diameter wire or a flexible, 0.035 inch×4.5 mm regular J guide-wire (which, as known to those skilled in the art is a guide wire having a single, J-shaped, flexible tip of 4.5 mm in length) to be inserted into the cannula and into the blood vessel. At that point, the cannula is removed leaving the guide wire in the blood vessel an extending outward through percutaneous puncture. The intra-vascular location of the guide wire is usually confirmed with fluoroscopy or other suitable method at this point.

Once confirmed that the guide wire is intra-vascular, a sheath and dilator may be passed over the guide wire. The dilator is then removed and the sheath is flushed with heparin. Once that is completed, a guide wire exchange may be made, whereby the general-purpose guide wire may be replaced with another guide wire. The new guide wire may be a long J guide wire, a long regular or firm, angled or straight, 0.035 inch guide wire or a long similar featured floppy-tipped stiff guide wire depending upon the physician, choice, and of any length that may be desired by the physician to accomplish whatever goal is required. On occasions for example in selected intra-aortic procedures, a very stiff wire, sometimes called a "coat-hanger" wire, such as a Lindquist or Amplatz wire is selected (for endo-vascular repair of an abdominal aortic aneurysm for example.)

Most medical guide wires presently come prepackaged in a single use sterile pack consisting of an outer layer on one side of the sterile pack, of white backing paper that is rugged and difficult to tear, and on the other side, transparent, non-tearable cellophane. The cellophane and the white backing paper are heat-sealed and at one end, a peelable seal is made. To open the sterile pack, the chevron seal is grasped between both hands and the two sheets of paper are peeled apart. The medical guide wire is then passed from the sterile pack to the operator.

Presently, a single medical grade guide wire is stored in a circular coil of a capillary plastic tube sufficient to contain the length of the guide wire that has been selected. Typically, the capillary tube is coiled and is four or five spirals wide (especially when longer guide wires are packaged). The wire resides within the lumen of the spiraled capillary tube. Each pass of the capillary tube passes inside its previous spiral and so on until the spiral stops at some point. Frequently, there is a separate 4–5 inch single tubular section of additional coil to restrain the end of the wire clipped inside the rest of the coil. Each coil of tube can move independently of the other coils of the tube. Thus, it is necessary to restrain the independent movement of each individual coil of the tube, which is typically accomplished by fastening the coils together with a plurality of individual, multi-toothed clips. Each clip typically has between 4 and 5 C-shaped extensions or teeth that are manually snapped or clipped onto each individual coil to hold the coils in place.

This system has several drawbacks. For example, the coils are easily deformable, thus the necessity of manually placing the clips onto the coils, and this process is labor and cost intensive. Also, the clips can and do come loose and thus the coiled tube may become uncoiled thereby threatening sterility during both use and transport, or the tube may simply become difficult to use in the operating room. Additionally, when the clipped, multi-coiled tube is gripped by the hand the coils tend to collapse on each other and the palm is not large enough to maintain a sufficient grip when that happens. This can and does complicate the removal of the guide wire from the tube. Additionally, it is necessary with this type of wire containment system to have an assembly line of workers placing individual clips symmetrically about the coiled capillary plastic tubing either before or after inserting the guide-wire. In addition, the plastic coil itself has to be extruded and then coiled before the clips can be applied. This type of containment system is labor intensive and therefore expensive to produce and clinically uncomfortable to use because the system is not designed with any ergonomic considerations.

Also, when removing the guide wire, the inner surface of the coiled plastic tubing and the guide wire bind with considerable friction and it is necessary to inject saline into the plastic tubing to reduce the friction and make extraction of the wire easier. Even when this is done the wire still has a tendency to bind and can be difficult to remove from the tube. Further, it is usually impractical to reinsert the guide wire into the plastic tube because the tube wall binds with the outer coil of the guide wire and friction prevents the wire from being reloaded. So, once the guide wire is removed from the tube, if not immediately used, the wire is placed in a bowl of saline under a laparotomy sponge or is simply placed under a wet lap until required. Sometimes during these procedures, the guide wire will spring loose and can become unsterile necessitating a new wire.

SUMMARY OF THE INVENTION

This invention is directed to a circular, coiled wire containment/dispenser system that is designed to simplify production methods and reduce production costs, and, because it is ergonomically designed, is easier to use with respect to the clinician. The circular body is preferably made of a single circle of semitransparent plastic, which contains one or more spiral grooves closed by a matching, clip on lid. There are preferably lateral and medial ramps or bumps on both sides of the spirals. These ramps deflect the wires toward the center of the spiral. Thus a large percentage of the surface of the wires are not touching the walls of the containment system and touch only the apexes of the medial and lateral ramps or bumps. By this method friction is greatly reduced to and both wire extraction and loading are facilitated.

In one embodiment, a guide wire containment apparatus is disclosed. The apparatus preferably comprises a body section and a spiral channel formed in the body section. The spiral channel preferably is defined by a first wall and a second wall. The spiral channel includes a plurality of indentations formed along each of the first wall and the second wall. The indentations direct a guide wire towards the center of the spiral channel.

The indentations further include an apex portion that makes contact with the guide wire. Because the guide wire only makes contact with the apex of the indentation of the spiral channel and not the spiral channel, the guide wire can be easily removed from the container.

A system for introducing a guide wire into a blood vessel is also disclosed. The system includes a guide wire container. The guide wire container comprises a body section and a spiral channel. The spiral channel is formed in the body section. A first wall and a second wall define the spiral channel. The spiral channel includes a plurality of indentations formed along the first wall and the second wall to direct a guide wire towards the center of the spiral channel. The system also includes a wire vise having a first and second end. Each end is operable to releasably secure the guide wire exiting the container. The second end includes a directing portion for guiding the guide wire into the blood vessel.

BRIEF DESCRIPTION OF THE DRAWINGS

Non-limiting and non-exhaustive preferred embodiments of the present invention are described with references to the following figures wherein like reference numerals refer to like parts throughout the various views unless otherwise specified:

FIG. 1 is a view of a guide wire container with lid on;

DETAILED DESCRIPTION OF PREFERRED EMBODIMENTS

An improved medical guide wire storage system, according to various aspects of the invention, provides for the convenient storage of medical guide wires. The guide wires are stored in a spiral channel. The spiral channel includes a plurality of indentations that contact portions of the inserted medical guide wire such that the medical guide wire is supported by pressing against the apexes of the indentations. This reduces the friction between the medical guide wire and the spiral channel, which makes the removal and reinsertion of the medical guide wire easier. Medical guide wire container may also include a handle portion through which the medical guide wire can be withdrawn.

For example, FIGS. 1–5 illustrate a guide wire container 100 in accordance with the teachings of the present invention. Container 100 comprises a housing 102. In one embodiment, housing 102 has a generally annular shape. Other shapes can be used, however, include a solid disk shape. A handle 106 is affixed to housing 102, preferably inside the now open section of the housing. A bridge section is attached to the outer section of the housing. Housing 102 is preferable made from alight weight plastic for ease of handling. Housing 102 can be made sufficiently wide to accommodate multiple guide wires.

Figure 1:
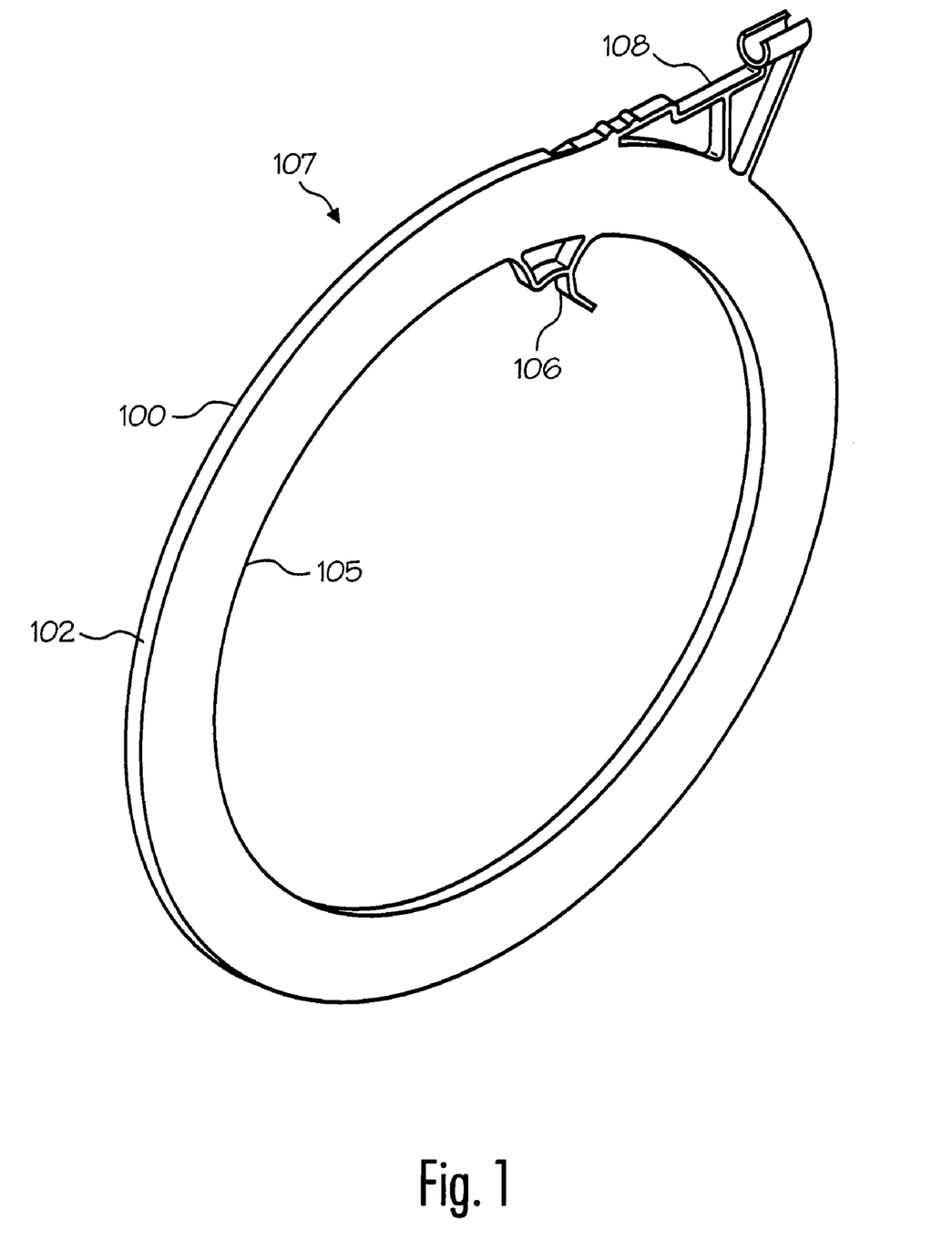
Figure 2:
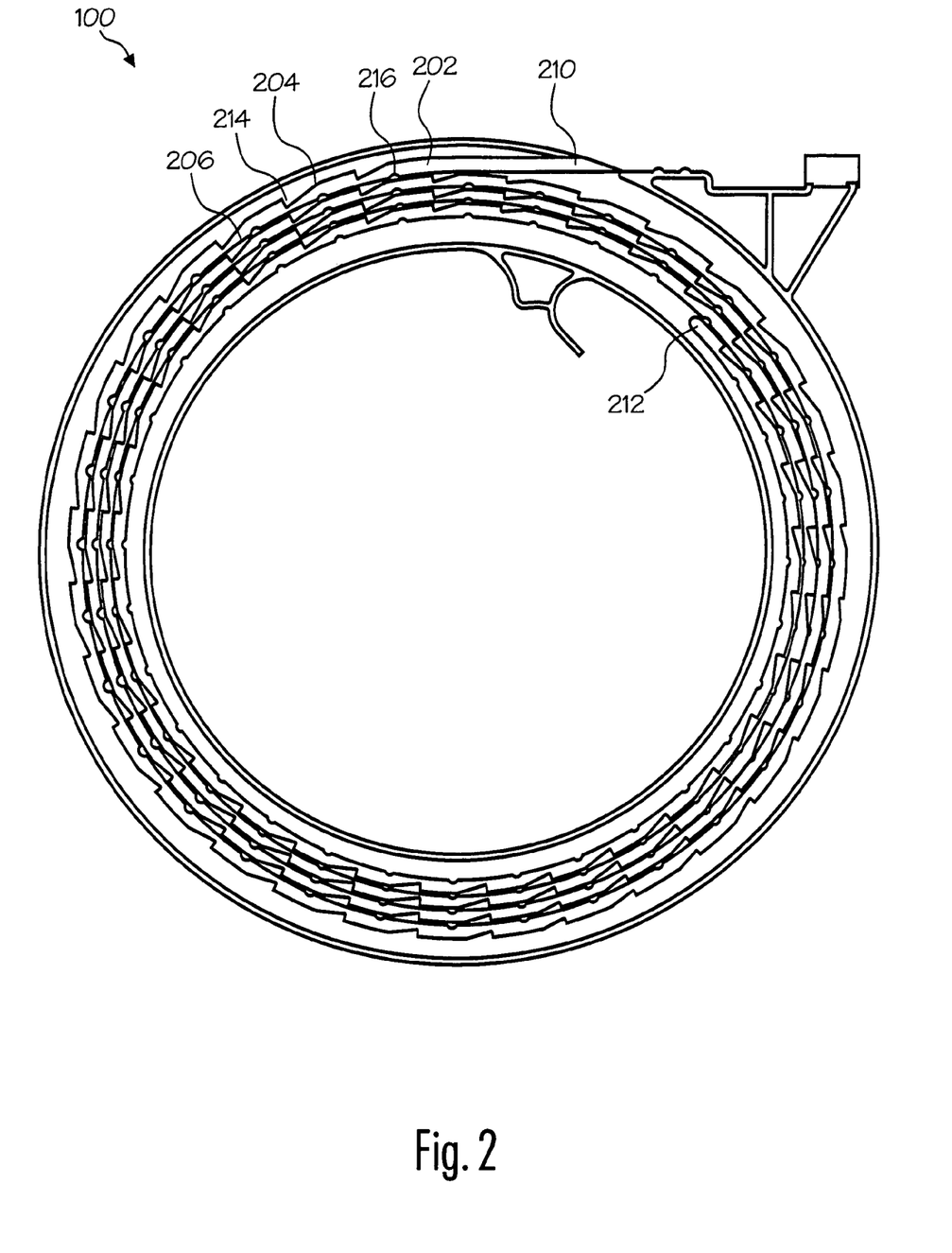
FIG. 2 is a plan view of the guide wire container.

Inside the housing 102 are one or more spiral channels 202 as seen in FIG. 2. Each spiral channel 202 has a first side 204 and a second side 206, between which define a central lumen 208. Spiral channel 202 starts at an initial point 210 and winds around the interior of housing 102 with a decreasing radius to a termination point 212. First side 204 includes a series of first side indentation 214 and second side 206 includes a series of second side indentation 216. First side indentation 214 and second side indentation 216 are designed to deflect an inserted guide wire towards the center of the spiral channel 202. FIG. 2 illustrates container 100 without lid 104. Lid 104 is typically secured on housing 102 and forms the top of the spiral channel 202. On the other side of housing 102, not seen in this drawing, can also have another spiral channel 202 and lid 104.

Figure 3:
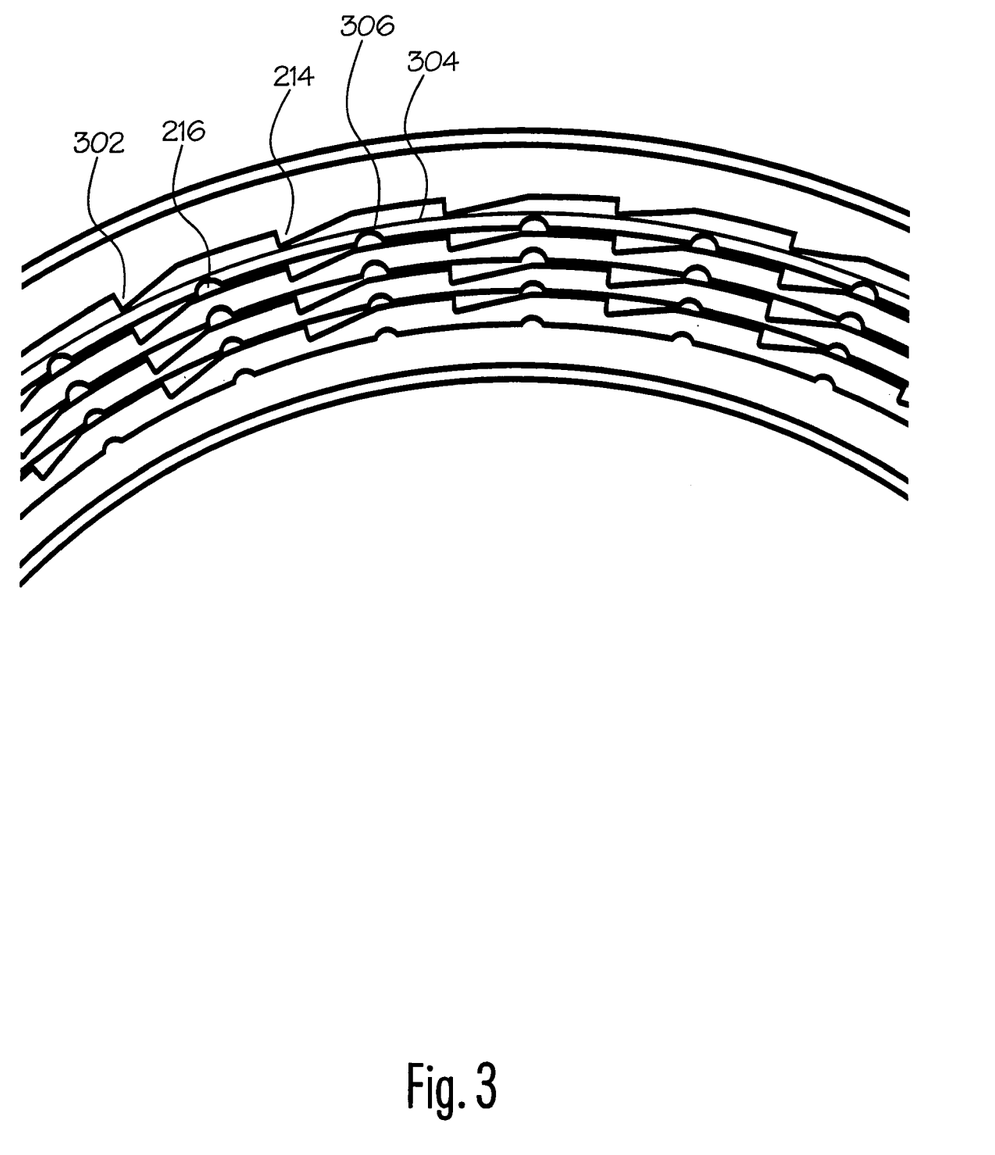
FIG. 3 is a close up illustration of the guide wire stored in the spiral channel.

In one embodiment, as best seen in FIG. 3, the first side indentations 214 are a series of ramps and the second side indentations 216 are a series of bumps. The apex 302 of the first side indentation 214 is touching the guide wire 304 at a point forward of where the top 306 of the second side indentation 216. That is, in this embodiment, the apexes 302 of the ramps are alternated with respect to the top 306 of the bumps. This arrangement deflects a guide wire 304 to the center of the spiral channel 202. The guide wire 304 touches just the apexes 302 of the ramps and tops of 305 of the bumps. Thus, only a very small portion of the spiral channel 202 contacts the guide wire 304. In one embodiment, only 1% of the surface of the guide wire 304 is in contact with the spiral channel 202. Since there are very few contact points, the coefficient of friction between the spiral channel 202 and the guide wire 304 is reduced to almost zero, facilitating both guide wire extraction and guide wire insertion. While first side indentation 214 is shown as a series of ramps and second side indentation 216 is shown as a series of bumps, both sides can have bumps or both sides can have ramps, or the bumps and ramps can be alternated on a side. Other shapes can be used as long as they deflect the guide wire 304 to the center of the spiral channel 202 and hold guide wire 304 with minimal points of contact.

Any type of medical guide wire 304 can be stored in and dispensed from container 100. Typical guide wires have a diameter between 0.010 and 0.038 inches and guide wire length exceeding 75 cm. The container can also accommodate guide wires of different stiffness as well as coated guide wires. Spiral channel 202 is preferably made from slippery or coated plastic to facilitate the removal of guide wires.

Some surgical procedures require the use of more than one guide wire, often of different design. The spiral channel 202 can be sized to accommodate multiple guide wires. Alternatively, multiple spiral channels 202 can be formed in housing 102. Each spiral channel 202 would hold a different guide wire 304. Thus, all of the guide wires necessary for a given surgical procedure can be stored in a single containment system 100. The guide wires 304 can then be extracted as needed. This avoids having many different containers for each guide wire 304 as well as being able to provide procedure specific containers.

Figure 4:
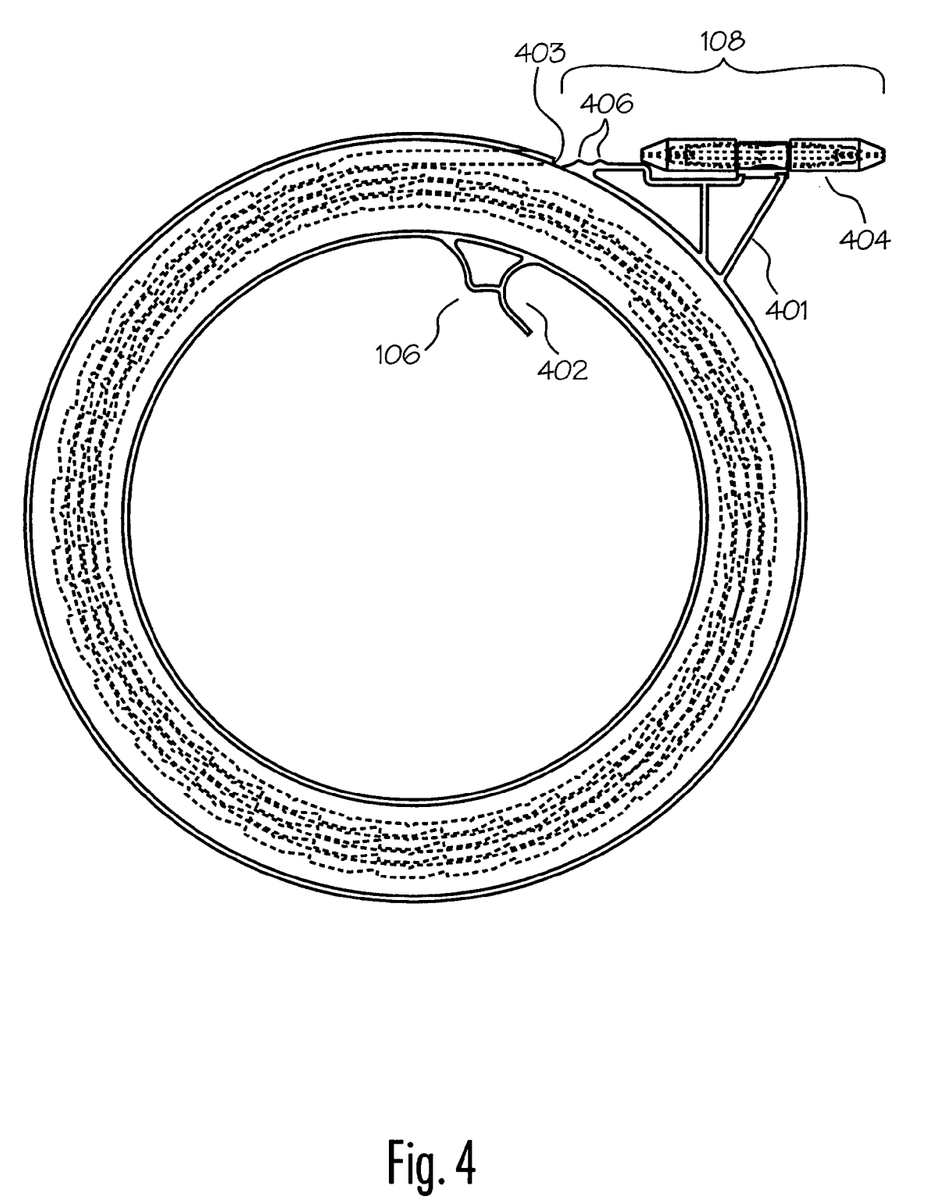
FIG. 4 is a view of the guide wire container with a wire vise attached.
Figure 5:
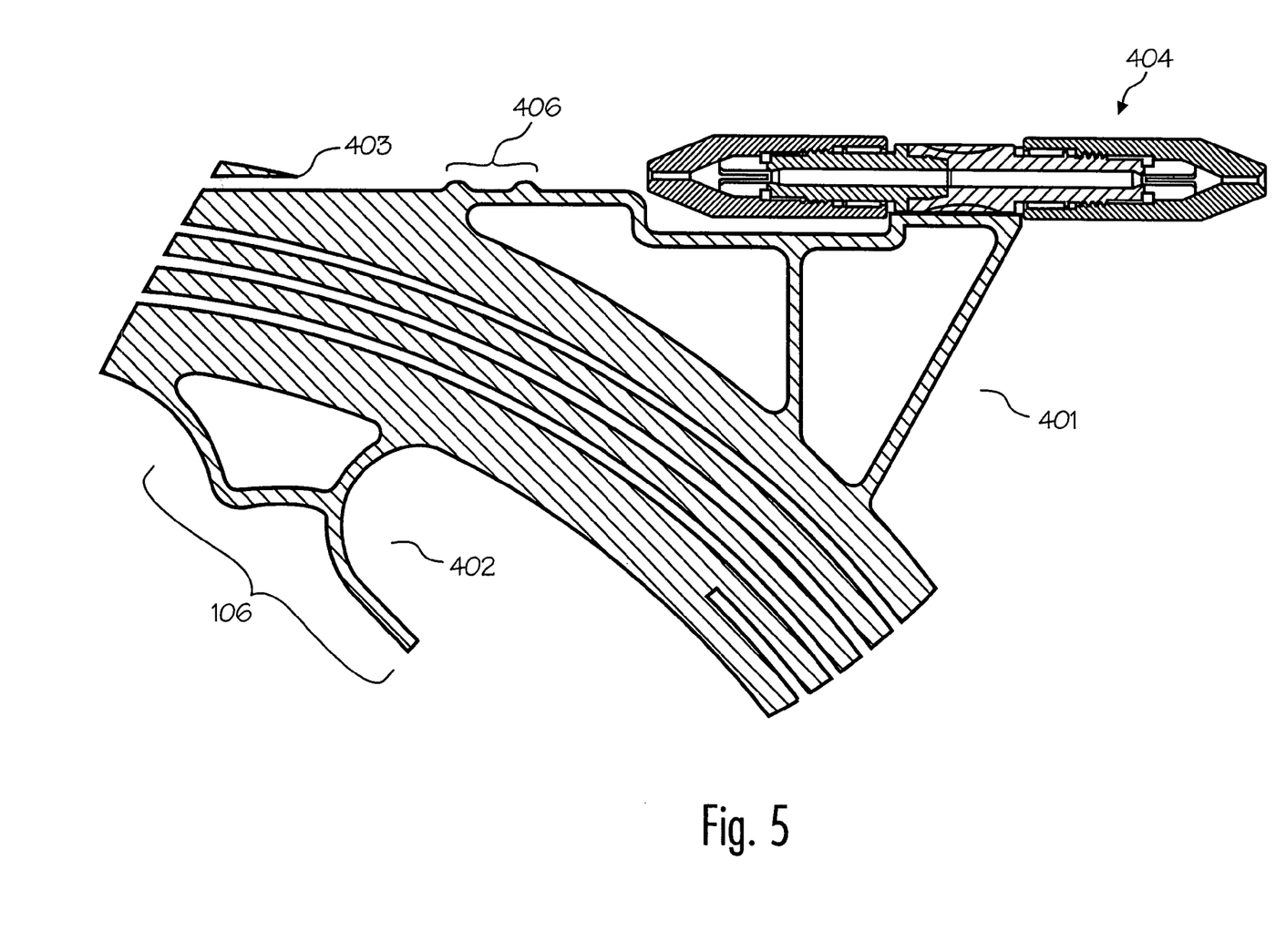
FIG. 5 is a close up view of the handle.
Figure 6:
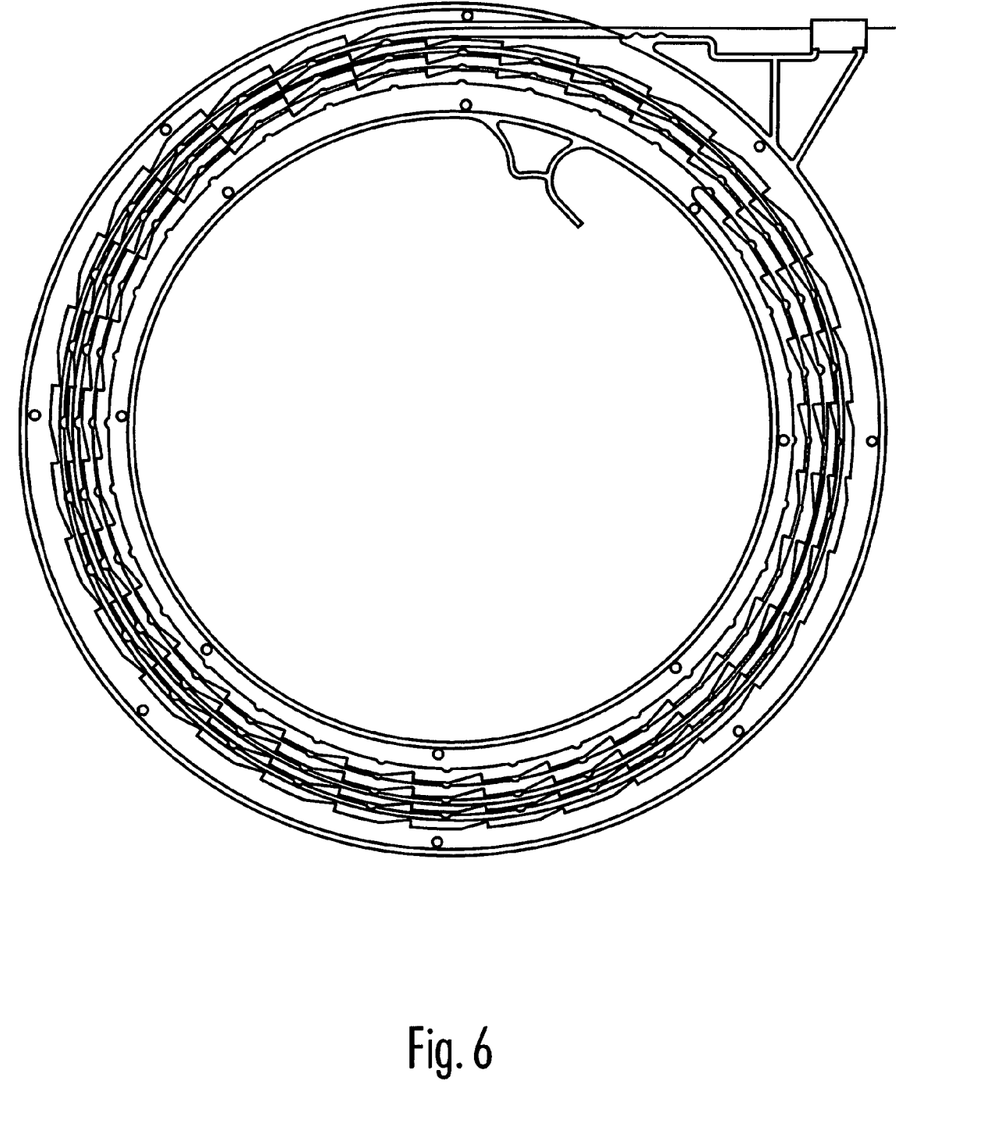
FIG. 6 is a top view of an assembled example of the invention.
Figure 7:
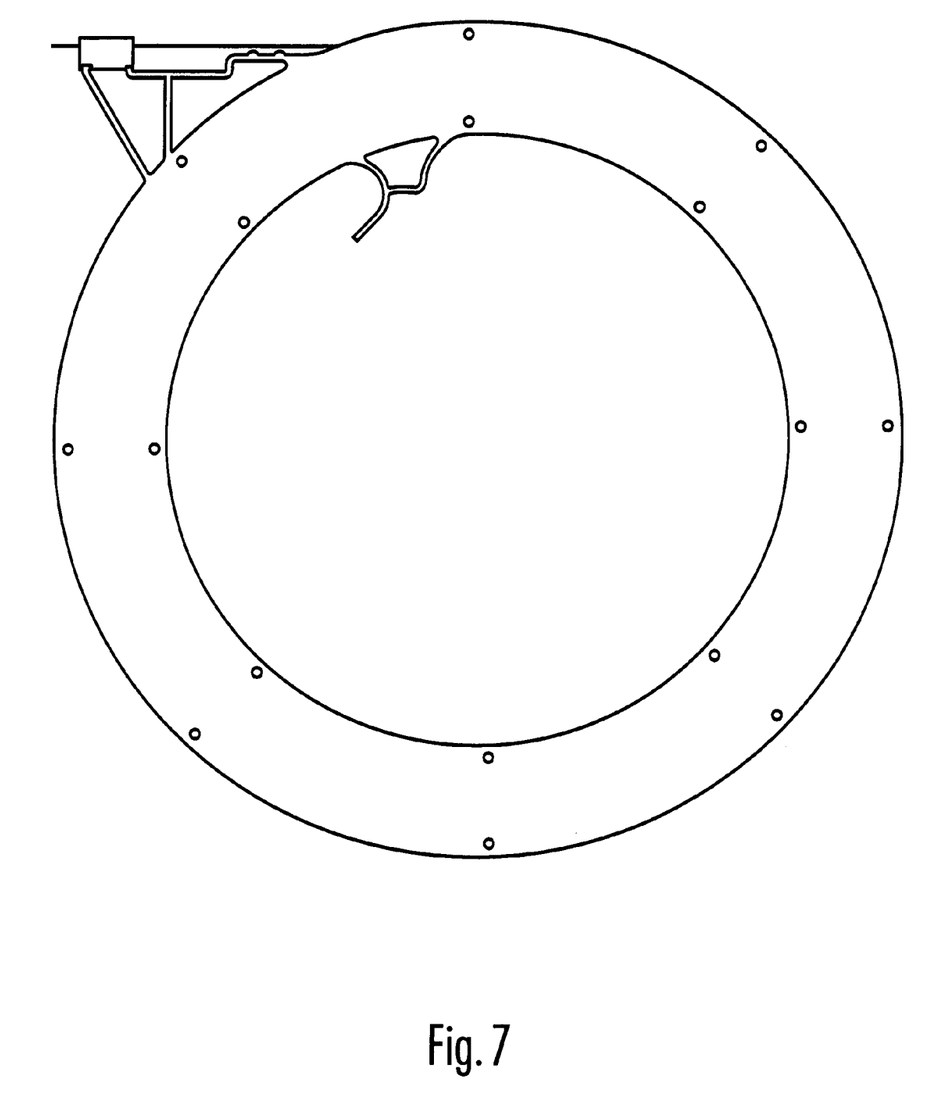
FIG. 7 is a bottom view of an assembled example of the invention.

As seen in FIGS. 4 and 5, there is a handle 106. At the bridge 108 there is a micro-lumen 403 for wire passage. The handle 106 as shown in FIG. 4, may have a series of trigger guards 402 to restrain several fingers of the user. The third section of the handle shown in FIG. 3, is the exit section, which acts as an exit pathway for the guide wire. It has a bridge mechanism to assist and simplify wire extraction. As the wire passes out from the spiral groove it passes over a bridge section of the dispenser. It then enters the wire vise/director/straightener section. The tip of this section then engages with the cannula in the blood vessel. By providing such an arrangement, unwanted movement of these fingers is arrested during thumb movements and overall there will be less motion artifact of the system. Because it helps to eliminate unwanted tremors, this will likely increase successful first time engagement of the wire into the cannula in the patient's blood vessel and diminish operator frustration trying to engage small orifices while the patient is bleeding from the open vascular cannula. It is possible that such a design will reduce patient overall blood losses, which can be significant with multiple wire exchanges that are often required in complex endo-vascular procedures.

Handle 106 includes a set of trigger guards 402 to rest the index, third and forth finger. These are ergonomically designed to reduce motion artifact of the human hand. This will reduce the tremor and encourage first time engagement of the wire and the cannula that will be in a patient's blood vessel and thereby bleeding at engagement. Such a system may lower patient blood loss. On the opposite side of the system is first a bridge 108 that permits the wire to pass out from the spiral on to a bridge section. The bridge section has two small ridges 406 designed to trap the wire between the thumb and the ridges. The wire is trapped in this location and while the thumb is moved forward the wire will then extrude out from the RACE without resistance. Optionally the bridge section may exist between the double collets of the dual grip torque device. The wire then optionally enters the dual action, bi-directional, wire vise 404. The wire then enters a wire director that is part of the dual action wire vise. The director straightens out the wire and facilitates wire engagement with the indwelling cannula. An example of a guide wire torque device is disclosed in co-pending application Ser. No. 10/444,773, filed May 24, 2003, entitled Guide Wire Torque Device, the disclosure of which is incorporated by reference.

Having now described preferred embodiments of the invention; modifications and variations to the present invention may be made by those skilled in the art. The invention is thus not limited to the preferred embodiments, but is instead set forth in the following clauses and legal equivalents thereof.

What is claimed is:

1. A guide wire containment apparatus comprising:
   a body section; and
   a spiral channel defined by a first wall and a second wall, the spiral channel formed in the body section, the spiral channel including a plurality of ramps formed along the first wall and a plurality of bumps formed along the second wall to direct a guide wire towards the center of the spiral channel.

2. The apparatus of claim 1 wherein the guide wire is held in place in the spiral channel by contacting an apex of each of the ramps.

3. The apparatus of claim 1 wherein multiple guide wires can be stored in the spiral channel.

4. The apparatus of claim 1 further comprising a second body section the second body section including a spiral channel storing at least one guide wire.

5. The apparatus of claim 1 further comprising a bridge section coupled to the body section, the bridge section comprising a ridge for securing the guide wire as it exits the container.

6. A container for storing and dispensing guide wire for use in medical procedures comprising:
   a body portion; and
   a spiral channel formed in the body portion, the spiral channel comprising:
   a central lumen defined by a first wall and a second wall; and
   steering means for directing a guide wire to the center of the lumen and away from the first wall and the second wall, the steering means including a plurality of ramps formed along the first wall and a plurality of bumps formed alone the second wall.

7. The container of claim 6 wherein the guide wire is held in place in the one or more spiral channels by contacting an apex of each of the ramps.

8. The container of claim 6 wherein multiple guide wires can be stored in each of the one or more spiral channels.

9. The container of claim 6 further comprising a second body section, the second body section including one or more spiral channels storing at least one guide wire.

10. The container of claim 6 further comprising a bridge section coupled to the body section, the bridge section comprising a ridge for securing the guide wire as it exits the container.

11. A system for introducing a guide wire into a blood vessel comprising:
   a guide wire container comprising:
   a body section; and
   a spiral channel defined by a first wall and a second wall, the spiral channel formed in the body section, the spiral channel including a plurality of ramps formed along the first wall and a plurality of bumps formed along the second wall to direct a guide wire towards the center of the spiral channel; and
   a wire vise having a first end and a second end, each end operable to releasably secure the guide wire exiting the container, the second end including a directing portion for guiding the guide wire into the a blood vessel.

* * * * *